US008435503B2

(12) United States Patent
Thorel et al.

(10) Patent No.: US 8,435,503 B2
(45) Date of Patent: May 7, 2013

(54) OPHTHALMIC AND OPHTHALMOLOGICAL USE OF A COMPLEX NUTRITIVE BASE IN AQUEOUS MEDIUM

(75) Inventors: Jean-Noël Thorel, Paris (FR); Hugues Gatto, Saint-Paul (FR)

(73) Assignee: Jean-Noel Thorel, Paris (FR)

( * ) Notice: Subject to any disclaimer, the term of this patent is extended or adjusted under 35 U.S.C. 154(b) by 2066 days.

(21) Appl. No.: 10/540,979

(22) PCT Filed: Dec. 26, 2003

(86) PCT No.: PCT/FR03/03917
§ 371 (c)(1),
(2), (4) Date: Aug. 8, 2005

(87) PCT Pub. No.: WO2004/060348
PCT Pub. Date: Jul. 22, 2004

(65) Prior Publication Data
US 2006/0103807 A1    May 18, 2006

(30) Foreign Application Priority Data
Dec. 26, 2002  (FR) ..................... 02 16722

(51) Int. Cl.
*A61K 31/74*    (2006.01)
(52) U.S. Cl.
USPC ..................................... 424/78.04
(58) Field of Classification Search ............... 424/78.04
See application file for complete search history.

(56) References Cited

U.S. PATENT DOCUMENTS

| | | | |
|---|---|---|---|
| 5,654,266 A | 8/1997 | Chen et al. | |
| 5,770,628 A | 6/1998 | Cantoro | |
| 5,942,218 A | 8/1999 | Kirschner et al. | |
| 6,194,457 B1 | 2/2001 | Braswell et al. | |
| 6,806,243 B2 * | 10/2004 | Hozumi et al. | 510/112 |
| 7,320,870 B2 * | 1/2008 | Laurie et al. | 435/7.1 |
| 2002/0034499 A1 | 3/2002 | Thorel et al. | |
| 2002/0049281 A1 | 4/2002 | Zhao et al. | |
| 2004/0057980 A1 | 3/2004 | Wagenaar | |
| 2004/0127699 A1 | 7/2004 | Zhao et al. | |

FOREIGN PATENT DOCUMENTS

| | | |
|---|---|---|
| EP | 0 468 122 A1 | 1/1992 |
| EP | 0 517 970 A1 | 12/1992 |
| EP | 0 698 388 A1 | 2/1996 |
| FR | 2 425 858 A1 | 12/1979 |
| JP | A-02-083318 | 3/1990 |
| JP | A-2002-020279 | 1/2002 |
| WO | WO 94/15649 A1 | 7/1994 |
| WO | WO 96/21421 A1 | 7/1996 |
| WO | WO 02/060495 A1 | 8/2002 |
| WO | WO 02/087326 A1 | 11/2002 |
| WO | WO 02087326 A1 * | 11/2002 |

OTHER PUBLICATIONS

Michael B. Berman; "Collagenase Inhibitors: Rationale for Their Use in Treating Corneal Ulceration"; *International Ophthalmogy Clinics*; vol. 15, No. 4; pp. 49-66; Jan. 1975; XP008011256.
Georges Bellon et al.; "Effects of preformed proline and proline amino acid precursors (including glutamine) on collagen synthesis in human fibroblast cultures"; *Biochimica et Biophysica Acta*; vol. 930; pp. 39-47; 1987; XP002290392.
Shambhu D. Varma; Scientific basis for medical therapy of cataracts by antioxidants[1,2]; *American Journal of Clinical Nutrition*; vol. 53, No. 1; pp. 335S-345S; 1991; XP009003151.
Steven T. Boyce, B.A., et al.; "Calcium-Regulated Differentiation of Normal Human Epidermal Keratinocytes in Chemically Defined Clonal Culture and Serum-Free Serial Culture"; *The Journal of Investigative Dermatology*; vol. 81, No. 1 Supplement; pp. 335-409; Jul. 1983.
Steven T. Boyce et al.; "Cultivation, Frozen Storage, and Clonal Growth of Normal Human Epidermal Keratinocytes in Serum-Free Media"; *Journal of Tissue Culture Methods*; vol. 9, No. 2; pp. 83-93; 1985.
J. C. Haffner et al.; "Inhibition of collagenase breakdown of equine corneas by tetanus antitoxin, equine serum and acetylcysteine"; *Vet. Ophthalmol.*; vol. 6, No. 1; pp. 67-72; Mar. 2003.
Kefalides N. A.; "Biosynthesis of Basement Membrane Collagen by Rabbit Corneal Endothelium in Vitro"; *Journal of; Biological Chemistry*; vol. 251, No. 3; pp. 730-733; Feb. 10, 1976.
Roger W. Beuerman et al.; "Ultrastructure of the Human Cornea"; *Microscopy Research and Technique*, vol. 33; pp. 320-335; 1996.
Oliver Doucet et al.; "A New In Vitro Human Epithelial Model for Assessing the Eye Irritating Potential of Formulated Cosmetic Products"; *In vitro and Molecular Toxicology*; vol. 11, No. 4; pp. 273-283; 1988.

\* cited by examiner

Primary Examiner — Jake M. Vu
(74) Attorney, Agent, or Firm — Oliff & Berridge, PLC

(57) ABSTRACT

The invention relates to a trophic composition in an aqueous medium comprising a complex nutritive base. The aforementioned base comprises, as a minimum, multiple amino acids, vitamins, trace elements and metallic salts, and is free of any cell growth factors, any biological extracts of animal or cell origin and any active therapeutic agents. The inventive composition is characterised in that, in addition to the complex nutritive base, it also comprises an inhibitor of the collagenases of corneal epithelium in humans or animals. The composition is further characterised in that it is formulated with the complex nutritive base in order to establish a pH of between 7.3 and 7.5 and an osmolarity of between 300 and 350 m Osm.

1 Claim, No Drawings

OPHTHALMIC AND OPHTHALMOLOGICAL USE OF A COMPLEX NUTRITIVE BASE IN AQUEOUS MEDIUM

The present invention relates to the ophthalmic and ophthalmologic use of a complex nutritive base both in man and in animals.

"Ophthalmic" in to be understood as meaning that a complex nutritive base as described and defined below may be utilized in various nontherapeutic applications in relation to the human or animal eye and, more specifically, in relation to the external surface or exterior of the cornea.

"Ophthalmologic" is to be understood as meaning that the same complex nutritive base may be utilized in the therapeutic or clinical treatment of the human or animal eye and, more specifically, for application, e.g. local application, in external contact with the cornea.

More specifically, for the purposes of the uses defined above, the present invention is concerned with trophic compositions comprising a complex nutritive base.

Complex nutritive base means any composition or formulation in an aqueous medium which differs from a cell culture medium in the manner specified below, even if, like the latter, it generally allows viable in-vitro culturing of an inoculum of certain predetermined cells for at least 72 h.

Various culture media have actually been described and are available commercially. Thus, in regard to the in-vitro culturing of keratinocytes, mention may be made of the following:

BOYCE S T, HAM R G, Calcium-regulated differentiation of normal human epidermal keratinocytes in defined clonal culture and serum-free serial culture; J. Invest. Dermatol. 1983; 81: 335-409;

BOYCE S T, HAM R G, Cultivation, frozen storage, and clonal growth of normal human epidermal keratinocytes in serum-free media; J. Tissue Culture Methods 1985; 9; 83-93;

the commercial medium known as MCDB 153, marketed by companies such as IRVINE SCIENTIFIC and GIBCO-BRL;

the commercial media known as DMEM (DUBECO Modified Epidermal Medium) and KSFM from GIBCO-BRL, etc.

To be effective, culture media of the above kind incorporate cellular growth factors, which may already be present in the composition of the culture medium at the outset or may be produced during culturing, e.g. by a feeder strain of fibroblasts, it being a question of the culturing of keratinocytes.

The use of a complex nutritive base of the kind considered in the case of the present invention does not involve growth factors, such as EGF (Epidermal Growth Factor) for example.

Many of the above-mentioned culture media include biological extracts, e.g. of animal, cellular, or other origin, i.e. ones obtained from a biological starting material. Examples of these biological extracts are any fetal calf serum and any bovine pituitary stalk extract.

By nature, these extracts are of varying, indeed uncertain composition.

A complex nutritive base of the kind considered in the case of the present invention does not include any biological extract as defined above.

In certain cases these same culture media mentioned above include various therapeutic active principles used as medicines, to aid the preservation and/or efficacy of the culture medium.

Examples of such active principles are certain antibiotics, e.g. penicillin and/or streptomycin, alone or in combination, and certain hormones, e.g. cholera toxin and insulin.

A complex nutritive base of the kind considered in the case of the present invention does not include any medicinal active principle.

Complex nutritive bases of this kind, in the sense of ones which may be used, alone or in combination with other constituents, as an active product or as an excipient, have been described in document WO 96/21421.

Complex nutritive bases of this kind comprise, in an aqueous medium, at least a multiplicity of amino acids, some of which are essential amino acids, various vitamins, trace elements, and metallic salts.

In document WO 96/21421, a complex nutritive base of this kind has, for example, the following composition, as shown in Table 1 below:

TABLE 1

| CONSTITUENTS | Concentration in mg/l |
|---|---|
| Water | q.s. |
| Amino acids | |
| L-Alanine | 9.2 |
| L-Arginine HCl | 421.4 |
| Amino acids (continued) | |
| L-Asparagine (anhydrous) | 14.2 |
| L-Aspartic acid | 4.0 |
| L-Cysteine HCl.H$_2$O | 42.0 |
| L-Glutamic acid | 14.8 |
| L-Glutamine | 1754.4 |
| Glycine | 7.6 |
| L-Histidine HCl.H$_2$O | 50.0 |
| L-Isoleucine | 6.0 |
| L-Leucine | 131.2 |
| L-Lysine HCl | 54.0 |
| L-Methionine | 13.5 |
| L-Phenylalanine | 10.0 |
| L-Proline | 34.6 |
| L-Serine | 126.1 |
| L-Threonine | 24.0 |
| L-Tryptophan | 9.3 |
| L-Tyrosine 2 Na 2H$_2$O | 11.7 |
| L-Valine | 70.3 |
| Vitamins | |
| d-Biotin | 0.02 |
| Folic acid | 0.80 |
| Nicotinamide | 0.04 |
| D-Ca pantothenate | 0.30 |
| Pyridoxine HCl | 0.06 |
| Riboflavin | 0.04 |
| Thiamine HCl | 0.30 |
| i-Inositol | 18.0 |
| Sodium pyruvate | 55.0 |
| Thymidine | 0.73 |
| Adenine (HCl) | 24.0 |
| DL-Lipoic acid | 0.20 |
| inorganic constituents | |
| Sodium chloride | 6800.0 |
| KCl | 112.0 |
| Na$_2$HPO$_4$ | 284.0 |
| CuSO$_4$.5H$_2$O | 0.003 |
| Sodium acetate | 300.0 (anhydrous) |
| D-Glucose | 1080.0 |
| HEPES (piperazine) | 6600.0 |
| Phosphorylethanolamine | 0.06768 |
| Ethanolamine | 0.04684 |
| Sodium sulfate | 3.4 |
| Sodium bicarbonate | 1160.0 |
| FeSO$_4$.7H$_2$O | 1.39 |
| MgCl$_2$.2H$_2$O | 120.0 |
| CaCl$_2$.2H$_2$O | 13.0–22.05 |

TABLE 1-continued

| CONSTITUENTS | Concentration in mg/l |
|---|---|
| $ZnSO_4 \cdot 7H_2O$ | 0.144 |
| $(NH_4)_6Mo_7O_{24} \cdot 4H_2O$ | 0.00120 |
| $Na_2SiO_3 \cdot 5H_2O$ | 0.142 |
| Inorganic constituents (continued) | |
| $MnCl_2 \cdot 4H_2O$ | 0.00002 |
| $SnCl_2 \cdot 2H_2O$ | 0.00011 |
| $NH_4VO_3$ | 0.00057 |

Document WO 02/087326 describes and proposes an ophthalmic and ophthalmologic composition comprising a vitamin derivative as a nonionic surfactant and a cationic agent or preservative, e.g. polyhexamethylene biguanide, and a disinfectant, e.g. hydrogen peroxide. This composition essentially cleans and disinfects, but does not regenerate the cornea.

Document U.S. Pat. No. 5,654,266 describes and proposes an essentially buffered saline composition for preserving and washing tissues prior to transplantation, e.g. corneas to be used for grafts. The proposed composition comprises mainly β-hydroxybutyrate, reducing the production and accumulation of lactic acid in the stored tissues.

Document EP 0 517 970 describes and proposes a solution for intraocular irrigation of the anterior and posterior chambers of the eye, for ocular surgery purposes, which repairs solely the corneal endothelium, i.e. the anterior chamber of the eye.

Document JP 02 083318 describes a composition which cleans the eye, comprising quaternary ammonium salts, chondroitin-sodium sulfate, glycyrrhetinic acid, and alcohols, including propylene glycol.

Document WO 026495 describes a composition for the care, and particularly the impregnation, of contact lenses, which contains vitamins, the aim being that the said composition be released from the impregnated contact lens on contact with the cornea.

The subject of the present invention is the ophthalmic or ophthalmologic use of a complex nutritive base as defined above, e.g. via a trophic composition comprising said base, notably to improve viability, e.g. under conditions of attack or stress, and to maintain the integrity and equilibrium of the epithelial cells of the cornea of the eye, in man or animals.

More specifically, the subject of the present invention is a use of the above kind to improve the viability, growth, and differentiation of corneal epithelial calls, in man or animals.

In the present invention, the trophic composition in an aqueous medium which may be utilized comprises:
  a complex nutritive base comprising at least a multiplicity of amino acids, vitamins, trace elements, and metallic salts, the said base being free of any cellular growth factor, any biological extract of animal or cellular origin, or any therapeutic active principle,
  an inhibitor of collagenases of the human or animal corneal epithelium, and
  a promoter of neocollagen synthesis.

Preferably the trophic composition is formulated with the complex nutritive base to establish a pH between 7.3 and 7.5 and an osmolarity between 300 and 350 mOsm.

Various collagenase inhibitors are already known, functionally and/or chemically; reference may be made to the following documents in particular:
  Berman; Int. Ophtalmol. Clin. 1975 Winter; 15(4): 49-66
  Haffner J C, Fecteau K A, Eilet H, Vet. Ophtalmol. 2003 March; 6(1): 67-72.

Various promoters of neocollagen synthesis are already known; reference may be made to the following documents in particular:
  Bellon G, Monboisse J C, Fandoux A, Borel J P, Biochim. Biophys. Acta. 1987 Aug. 19, 930 (1); 39-47
  Kefalides N A, Cameron J D, Tomicheck E A, Yanoff M, J Biol Chem. 1976 Feb. 10; 251(3): 730-3.

According to the invention, the trophic composition benefits from the following characteristics, the latter being considered alone or in combination:
  the inhibitor of collagenases is chosen from the group comprising cysteine, N-acetylcysteine, and EDTA calcium salt;
  the inhibitor of collagenases is N-acetylcysteine;
  the inhibitor of collagenases represents at most 5% and preferably between 0.05 and 0.5% by weight of the said composition;
  the promoter of neocollagen synthesis is proline or hydroxyproline;
  the promoter of neocollagen synthesis represents at most 0.5% and preferably 0.004% by weight of the said composition;
  the trophic composition comprises hyaluronic acid and/or a salt of hyaluronic acid in a total proportion by weight of the composition of at most 0.1% and preferably 0.07%;
  the trophic composition includes a preservative in a proportion by weight of the composition of at most 0.0001%;
  the preservative is polyhexanide or polyhexamethylene biguanide (PHMB);
  the trophic composition corresponds to the formula described by Table 2 in the description.

Compared to the composition as per Table 1, the composition as per Table 2 differs from the latter in the following respects:
  it does not include vitamin B12, putrescine 2HCl, or $Na_2SiO_3$
  it includes both a collagenase inhibitor and a promoter of neocollagen synthesis
  its pH and osmolarity characteristics allow oxygenation of the corneal epithelium and tear lysozyme activity.

The invention also relates to the use of a trophic composition as described above as an ophthalmologic and contactologic medicine in man or animals, by application, e.g. local application, in external contact with the cornea.

It also relates to such a medicine in liquid form or in dry form, that is to say for reconstitution with an aqueous medium.

In one variant, such a medicine is in liquid form, e.g. in the form of drops, or regenerating tears, or eyewash, or solution.

Thus, as an example, the present invention proposes an eyewash comprising a trophic composition as defined above, which can heal the cornea or prevent conjunctival adhesions.

Such an eyewash has the following indications:
  corneal ulcers of traumatic or other origin, corneal burns;
  prevention of conjunctival adhesions and corneoconjunctival adhesions (symblepharon);
  conjunctival and corneal xerosis.

The invention also relates to an ophthalmic solution, e.g. comfort solution, for local application in external contact with the cornea in man or animals, comprising for example a trophic composition as defined above.

Thus the present invention proposes, for example, "regenerating tears" comprising a trophic composition as defined above for the hydration of contact lenses and regeneration of the cornea in man or animals.

"Regenerating tears" of this kind also lubricate the cornea at the same time. In the final analysis, they prevent or limit premature erosion of the cornea as a result of the action of contact lenses, hard or semi-rigid ones in particular. These "regenerating tears" both improve visual comfort and increase the length of time for which contact lenses can be worn.

Thus the present invention proposes, for example, comfort drops for the following uses:
- ocular dryness of iatrogenic origin (associated, in particular, with the use of topical or systemic retinoids, antihistamines, antiparkinsonian drugs, beta blockers, spasmolytics, anxiolytics, neuroleptics, antidepressants, and bronchodilators, etc.), producing discomfort, particularly in patients who wear contact lenses;
- ocular dryness in the elderly.

The invention also relates to the use of a complex nutritive base as defined above for the treatment, e.g. the preservation, of items or prostheses, such as contact lenses, which are designed to come into external contact with the cornea of the eye in man or in animals.

It relates, in this regard, to a solution for the preservation, or storage, or transport, or use (e.g. surgical use) of items or prostheses, such as contact lenses, which are designed to come into external contact with the cornea of the eye in man or in animals.

Thanks to a complex nutritive base as defined above, and, in particular, to a trophic composition in accordance with the present invention, and as demonstrated by the studies described below, the primary intrinsic properties of the corneal epithelium are preserved for a long time and, at the same time, its resistance to attack is increased and, where applicable, its return to a state of equilibrium promoted.

The present invention is now described and exemplified on the basis of a trophic composition in an aqueous medium with the formula shown in Table 2.

TABLE 2

| Line No. | International Nomenclature Cosmetic Ingredient name (INCI name) | Concentration in mg/l |
| --- | --- | --- |
| 1 | WATER | q.s. |
| 2 | SODIUM CHLORIDE | 6800 |
| 3 | GLUTAMINE | 1754.4 |
| 4 | SODIUM BICARBONATE | 1160 |
| 5 | GLUCOSE | 1080 |
| 6 | ARGININE HCL | 421.4 |
| 7 | SODIUM ACETATE | 300 |
| 8 | DISODIUM PHOSPHATE | 284 |
| 9 | LEUCINE | 131.2 |
| 10 | SERINE | 126.1 |
| 11 | Mg CHLORIDE | 120.0 |
| 12 | K CHLORIDE | 112 |
| 13 | VALINE | 70.3 |
| 14 | SODIUM PYRUVATE | 55 |
| 15 | LYSINE HCL | 54 |
| 16 | HISTIDINE HCL | 50 |
| 17 | CYSTEINE HCL | 42 |
| 18 | ADENINE | 24 |
| 19 | THREONINE | 24 |
| 20 | Ca CHLORIDE | 20.05 |
| 21 | INOSITOL | 18 |
| 22 | GLUTAMIC ACID | 14.8 |
| 23 | ASPARAGINE | 14.2 |
| 24 | METHIONINE | 13.5 |
| 25 | TYROSINE | 11.7 |
| 26 | PHENYLALANINE | 10.0 |
| 27 | TRYPTOPHAN | 9.3 |
| 28 | ALANINE | 9.2 |
| 29 | GLYCINE | 7.6 |
| 30 | ISOLEUCINE | 6.0 |
| 31 | ASPARTIC ACID | 4.0 |
| 32 | SODIUM SULFATE | 3.4 |
| 33 | FERROUS SULFATE | 0.003 |
| 34 | FOLIC ACID | 0.8 |
| 35 | THYMIDINE | 0.73 |
| 36 | CYANOCOBALAMIN | 0.41 |
| 37 | CALCIUM PANTOTHENATE | 0.3 |
| 38 | THIAMINE HCL | 0.3 |
| 39 | THIOCTIC ACID | 0.3 |
| 40 | ZINC SULFATE | 0.144 |
| 41 | SODIUM SILICATE | 0.142 |
| 42 | PYRODIXINE HCL | 0.06 |
| 43 | NIACINAMIDE | 0.04 |
| 44 | RIBOFLAVIN | 0.3 |
| 45 | BIOTIN | 0.02 |
| 46 | COPPER SULFATE | 0.003 |
| 47 | AMMONIUM MOLYBDATE | 0.00120 |
| 48 | AMMONIUM VANADATE | 0.003 |
| 49 | Mn CHLORIDE | 0.00002 |
| 50 | SODIUM HYALURONATE | 70 |
| 51 | POLYHEXANIDE or POLYHEXAMETHYLENE BIGUANIDE | 0.1 |
| 52 | N-ACETYLCYSTEINE | 500 |
| 53 | HYDROXYPROLINE or PROLINE | 35 |

In line with the definition of the trophic composition in accordance with the present invention, the ingredients of the complex nutritive base in an aqueous medium are all those numbered 1-49, whilst ingredients 50-53 are considered not to form part of the complex nutritive base, and serve to make it suitable for external contact with the corneal epithelium of the eye.

Ingredients 50 and 51 are optional, depending on the role or function sought for the trophic composition.

Moreover, the choice and proportions of the various ingredients are defined so as to establish, in the final trophic composition:
- a pH between 7.3 and 7.5 and preferably between 7.42 and 7.45 (a pH which promotes oxygenation of the corneal epithelium and tear lysozyme activity);
- an osmolarity between 300 and 350 mOsm, 340 mOsm for example.

Study 1

This evaluates the biocompatibility of the trophic composition defined above in a reconstituted human corneal epithelium model.

Starting from the formula shown in Table 2, four variants are defined and formulated, namely:
- EVE 1: without sodium hyaluronate (ingredient 50) and without preservative (ingredient 51).
- EVE 2: without sodium hyaluronate (ingredient 50) but with preservative (ingredient 51).
- EVE 3: with sodium hyaluronate (ingredient 50) but without preservative (ingredient 51).
- EVE 4: identical to the formula shown in Table 2, i.e. with sodium hyaluronate (ingredient 50) and with preservative (ingredient 51).

Minor adjustments are made to the other ingredients in order to keep the pH and osmolarity within the values stated above.

The cytocompatibility of formulas EVE 1 to EVE 4 is evaluated by topical application using an in-vitro reconstructed human corneal epithelium model of the kind available from SKINETHIC LABORATORIES, 45 Rue Saint Philippe, 06000 NICE, France.

Roger W. BEUERAN and Lia PEDROSA have described in detail the ultrastructure of the human cornea in an article entitled "Ultra-structure of the human cornea" in the journal "Microscopy Research and Technique", 33: 320-335 (1996), to which reference should be made as required.

Starting from the natural structure, O. DOUCET et al. have proposed and described a reconstructed, three-dimensional, human corneal epithelium, for the performance of various in-vitro toxicity studies in particular; cf. the article entitled "A new in vitro human epithelium model for assessing the eye irritation potential of formulated cosmetic products" published in "In vitro and Molecular Toxicology", 11, 4: 273-283 (1998).

This reconstructed corneal epithelium, or model, is obtained by culturing corneal epithelial cells, such as the HCE line available from and marketed by LSU Eye Center, Louisiana State University School of Medicine, New Orleans, La., 70112 USA. The epithelial cells are cultured at the air/liquid interface in a defined medium and they form a corneal epithelial tissue, without a stratum corneum, which is close to the corneal epithelium in vivo.

The study is carried out in reconstructed corneal epithelia of this kind as obtained on the $5^{th}$ day of culturing (size: 0.5 cm$^2$), the quality control of the various epithelia at the various stages of culturing being undertaken by the aforementioned SKINETHIC LABORATORIES, in accordance with the last cited publication.

The test principle consists in applying the trophic composition in direct contact with the reconstructed corneal epithelium for 15 minutes, three times a day, for a period of 7 days. An untreated control corneal epithelium is run in parallel. Each condition (except for the untreated control) is carried out in duplicate. On the $2^{nd}$, $4^{th}$, and $7^{th}$ days of the study, cell viability (MTT test) is evaluated for each of the conditions.

In practice, 30 µl of the trophic compositions to be tested is placed directly on the surface of the corneal equivalents 3 times a day (at 09:00, 13:00, and 17:00) for 15 minutes in each case. After this contact period, excess composition is removed and the epithelia are incubated at 37° C., in a humid atmosphere, 5% $CO_2$. This operation is repeated every day for 7 days. On the $2^{nd}$, $4^{th}$, and $7^{th}$ days of the study, samples of the reconstructed epithelia are collected for the cell viability test.

On the $2^{nd}$, $4^{th}$, and $7^{th}$ days of the study, the epithelia samples are rinsed with PBS and placed in 300 µl of MTT (0.5 mg/ml). After 3 hours' incubation at 37° C., 5% $Co_2$, the epithelia are transferred into 1.5 ml isopropanol. The MTT cleavage product is extracted with gentle stirring over a period of 2 h at room temperature. The optical density at 570 nm is then measured in 200 µl of extraction solution. The results are expressed as percentage viability compared to the (untreated) control:

$$\% \text{ viability} = [OD_{(570 \text{ nm test product})} / OD_{(570 \text{ nm control})}] \times 100$$

Under the experimental conditions defined, the viability of the reconstructed human corneal epithelia in vitro is fully maintained after topical application of each of the aforementioned trophic compositions. The presence of the preservative and of hyaluronic acid at the specified concentrations of use does not have any effect on the cellular viability of the epithelia, which is maintained.

Study 2

A reconstituted human corneal epithelium is cultured in the trophic compositions defined above and the results obtained are compared with those obtained from culturing in a buffered saline solution.

The chosen corneal epithelium model is identical to the one described and defined in Study 1 and is cultured for 72 h in the trophic composition being investigated.

Just one trophic composition is used for this study, namely the one specified in Table 2 and referred to as EVE 4 in Study 1.

As soon as the epithelia are received, the SKINETHIC nutritive transport medium is removed, and replaced, in the case of one of the epithelia, with 1 ml of the trophic composition being investigated. A second epithelium is placed in a buffered saline solution (Phosphate Buffered Saline, PBS, $Ca^{2+}$- and $Mg^{2+}$-enriched) for comparison. The cytocompatibility of the trophic composition being investigated has previously been verified (no cytotoxic effect, cf. preceding study, Study 1). The epithelia are incubated at 37° C., in a humid atmosphere, 5% $CO_2$. The media are replaced every day. After 3 days of culturing, samples of the 2 reconstructed epithelia are collected for histological analysis. They are fixed with a 10% formaldehyde solution and then embedded in paraffin. The histology of the hematoxylin/eosin-stained sections is evaluated under an optical microscope.

The histopathological interpretation of the sections includes the thickness and regularity of the epithelial tissue and also the morphology, cohesion, and proliferative capacity of the cells.

As regards the epithelium cultured in the trophic composition for 72 h, analysis of the sample shows an epithelium implanted on the membranal support. It comprises 6 to 7 layers of closely packed cells (the connecting bridges are visible). There is no sign of necrosis or of keratinization of the superficial layer.

In the case of the epithelium cultured in a buffered saline solution for 72 h, analysis of the sample shows the near-total disappearance of the epithelium; only the support is visible. There is no identifiable cell layer.

Under the experimental conditions defined for this study, a reconstructed human corneal epithelium cultured for 72 h in a trophic composition in accordance with the present invention survives and exhibits cellular cohesion. In contrast, in the similar experiment carried out with a buffered saline solution, there is complete degeneration of the epithelium, which is no longer identifiable.

Study 3

The healing properties of trophic compositions in accordance with the invention are evaluated in a reconstituted human cornea model.

The four variants of the trophic composition investigated are identical to those defined and described in Study 1.

The reconstructed corneal epithelium model is identical to that described and defined in Studies 1 and 2.

The healing properties of the trophic compositions investigated are evaluated after topical application in the aforementioned model, in which a mechanical lesion is created beforehand.

The lesions in the surface of the reconstructed corneal epithelia are created with the tip of a scalpel, each of the epithelia being divided along its diameter.

The test principle consists in applying the trophic composition in direct contact with the reconstructed corneal epithelium for 15 mins, three times a day, every day for a period of 9 days, starting immediately after the creation of the lesions. A control in buffered saline solution (PBS) is run in parallel.

On the $2^{nd}$, $4^{th}$, $7^{th}$, and 9 days of the study, the histology of the reconstructed tissue is evaluated for each of the conditions. It is compared with the histology of a control, comparison condition corresponding to an untreated, undamaged epithelium.

In practice, 30 µl of the trophic compositions to be tested is placed directly on the surface of the corneal epithelia 3 times a day (at 09:00, 13:00, and 17:00) for 15 mins in each case. After this contact period, excess composition is removed and the epithelia are incubated at 37° C., in a humid atmosphere, 5% $CO_2$. This operation is repeated every day for 9 days. On the $2^{nd}$, $4^{th}$, $7^{th}$, and $9^{th}$ days of the study, samples of the reconstructed epithelia are collected for histological analysis.

On the $2^{nd}$, $4^{th}$, $7^{th}$, and $9^{th}$ days of the study, the epithelia ate fixed with a 10% formaldehyde solution and then embedded in paraffin. The histology of the haematoxylin/eosin-stained sections is evaluated under an optical microscope.

The healing properties of the trophic compositions are evaluated by histological analysis of the sections and observation of epithelial repair at the site of the lesion created by the scalpel. The site of the lesions is marked with India ink on the surface of the corneal epithelia before histological section (transverse section of the epithelium).

The histopathological interpretation of the sections includes the thickness and regularity of the epithelial tissue and also the morphology, cohesion, and proliferative capacity of the cells after the creation of the lesion.

Combined photographs establish, for each condition, the transverse sections of the epithelia performed at the start of treatment ($2^{nd}$ day after the creation of the lesion) and on the last day of treatment ($9^{th}$ day).

In the case of the (untreated, undamaged) Control, a vital epithelium consisting of 6 to 7 layers of closely packed, regularly shaped cells (with appearance of pavement cells) is observed on the $2^{nd}$ day of culturing. On the $9^{th}$ day of treatment there is observable thickening of the epithelium, which is made up of around ten layers of cells, which are still closely packed and regular. A keratinized layer is seen at the surface.

In the case of the treatment with EVE 4 (trophic composition in accordance with Table 2), the photograph taken on the $2^{nd}$ day shows the lesion created in the epithelium exposing the membranal support. The epithelium is vital on both sides of the wound. There is no keratinization. On the $9^{th}$ day of treatment a continuous, repaired epithelium made up of several layers of non-necrosed, relatively regular cells (which look more rounded than in the case of the Control) is observable at the site marked with India ink. An area of keratinization is seen in the superficial layers.

In the case of the treatment with a buffered saline solution (PBS), the damaged area, marked by a considerable loss of epithelial substance, is observable on the $2^{nd}$ day. On the $9^{th}$ day, a repaired epithelium made up of only 5 to 6 layers of cells is observable at the site marked, the cells having a rounded and in some instances a turgescent appearance, with vacuoles.

In the case of the treatment with compositions EVE 1, EVE 2, and EVE 3, a lesion marked out by a complete loss of substance is observable in the samples collected on the $2^{nd}$ day of the study. On both sides, the epithelium has many layers and is vital and not keratinized.

On the $9^{th}$ day, in the case of the EVE 1 formulation, a continuous reconstituted epithelium made up of rounded, fairly regular cells with a number of vacuoles is observable. In the case of the EVE 2 and EVE 3 formulations, the epithelia look identical with closely packed, morphologically regular cells.

However, the epithelia seem to be thinner than those treated with the EVE 4 formulation.

Under the experimental conditions defined, repair of the previously damaged human corneal epithelia is observable at the end of the treatments in each of the conditions tested.

The EVE 4 formulation (containing hyaluronic acid and preservative) gives the best results. The repaired epithelium is continuous, vital, has many layers, and is made up of closely packed, regular cells.

Study 4

The healing properties of trophic compositions in accordance with the present invention are evaluated in comparison with a buffered saline solution.

The trophic composition investigated is identical to the one defined in Table 2.

The reconstructed corneal epithelium model is identical to that used in Studies 1 to 3.

The healing properties of the trophic compositions are evaluated by topical application in an in-vitro reconstructed human corneal epithelium model, in which a mechanical lesion is created beforehand.

The lesions in the surface of the reconstructed corneal epithelia are created with the tip of a scalpel, each of the epithelia being divided along its diameter.

The test principle consists in applying the trophic composition in direct contact with the reconstructed corneal epithelium for 15 mins, three times a day, every day for a period of 7 days, starting immediately after the creation of the lesions. A control in buffered saline solution ($Ca^{2+}$- and $Mg^{2+}$-enriched PBS) is run in parallel. On the $2^{nd}$, $4^{th}$, and $7^{th}$ days of the study, the histology of the reconstructed tissue is evaluated for each of the conditions. It is compared with the histology of a control, comparison condition corresponding to an untreated, undamaged epithelium.

In practice, 30 µl of the compositions to be tested is placed directly on the surface of the corneal equivalents 3 times a day (at 09:00, 13:00, and 17:00) for 15 mins in each case. After this contact period, excess composition is removed and the epithelia are incubated at 37° C., in a humid atmosphere, 5% $CO_2$. This operation is repeated every day for 7 days. On the $2^{nd}$, $4^{th}$, and $7^{th}$ days of the study, samples of the reconstructed epithelia are collected for histological analysis.

On the $2^{nd}$, $4^{th}$, and $7^{th}$ days of the study, the epithelia are fixed with a 10% formaldehyde solution and then embedded in paraffin. The histology of the hematoxylin/eosin-stained sections is evaluated under an optical microscope.

The healing properties of the trophic compositions are evaluated by histological analysis of the sections and observation of epithelial repair at the site of the lesion created by the scalpel. The site of the lesions is marked with India ink on the surface of the corneal epithelia before histological section (transverse section of the epithelium).

The histopathological interpretation of the sections includes the thickness and regularity of the epithelial tissue and also the morphology, cohesion, and proliferative capacity of the cells after the creation of the lesion.

Photographs establish, for each condition, the transverse sections of the epithelia performed at the various stages of treatment.

In the case of the (untreated, undamaged) Control, a vital epithelium consisting of 6 to 7 layers of closely packed, regularly shaped cells (with appearance of pavement cells) is observed on the $2^{nd}$ day of culturing. On the $7^{th}$ day of treatment there is observable thickening of the epithelium, which is made up of around ten layers of cells, which are still closely packed and regular. A keratinized layer is seen at the surface.

In the case of the treatment with the trophic composition shown in Table 2, the photograph taken on the $2^{nd}$ day shows the lesion created in the epithelium exposing the membranal support. The epithelium is vital on both sides of the wound. There is no keratinization. On the 4$^{th}$ day, cellular recolonization of the support is observed. The epithelium is made up of 3 to 4 layers of cells, some of which are in the process of division. On the 7$^{th}$ day of treatment a continuous, repaired epithelium made up of several layers of non-necrosed, relatively regular cells (which look more rounded than in the case of the Control) is observable at the site marked with India ink. An area of keratinization is seen in the superficial layers.

In the case of the treatment with a buffered saline solution (PBS), the damaged area, marked by a considerable loss of epithelial substance, is observable on the 2$^{nd}$ day. On the 4$^{th}$ day the epithelium re-forms, consisting of only one to two layers of rounded cells. On the 7$^{th}$ day, the epithelium is repaired and is made up of 5 to 6 layers of cells, these having a rounded and in some instances a turgescent appearance, with vacuoles.

Under the experimental conditions defined, the trophic composition allows the reconstitution of a previously damaged human corneal epithelium. The repaired epithelium is continuous, vital, has many layers, and is made up of closely packed, regular cells.

The application of a buffered saline solution likewise allows repair of the epithelium. However, the latter is made up of only 3 to 4 layers of cells, demonstrating that the regeneration is inferior to that observed with the trophic composition. Moreover, the cells are rounded, with a number of vacuoles.

The invention claimed is:

1. A process to improve viability, growth, and differentiation of corneal epithelial cells, the process comprising:
applying a trophic composition to an external surface of a cornea of an eye of a human or an animal, wherein the trophic composition has a pH between 7.3 and 7.5 and an osmolarity between 300 and 350 mOsm and the trophic composition comprises the following components:

| Component | Concentration (mg/L) |
| --- | --- |
| Water | q.s. |
| Sodium chloride | 6800 |
| Glutamine | 1754.4 |
| Sodium bicarbonate | 1160 |
| Glucose | 1080 |
| Arginine HCl | 421.4 |
| Sodium acetate | 300 |
| Disodium phosphate | 284 |
| Leucine | 131.2 |
| Serine | 126.1 |
| Mg chloride | 120.0 |
| K chloride | 112 |
| Valine | 70.3 |
| Sodium pyruvate | 55 |
| Lysine HCl | 54 |
| Histidine HCl | 50 |
| Cysteine HCl | 42 |
| Adenine | 24 |
| Threonine | 24 |
| Ca chloride | 20.05 |
| Inositol | 18 |
| Glutamic acid | 14.8 |
| Asparagine | 14.2 |
| Methionine | 13.5 |
| Tyrosine | 11.7 |
| Phenylalanine | 10.0 |
| Tryptophan | 9.3 |
| Alanine | 9.2 |
| Glycine | 7.6 |
| Isoleucine | 6.0 |
| Aspartic acid | 4.0 |
| Sodium sulfate | 3.4 |
| Ferrous sulfate | 0.003 |
| Folic acid | 0.8 |
| Thymidine | 0.73 |
| Cyanocobalamin | 0.41 |
| Calcium pantothenate | 0.3 |
| Thiamine HCl | 0.3 |
| Thioctic acid | 0.3 |
| Zinc sulfate | 0.144 |
| Sodium silicate | 0.142 |
| Pyrodixine HCl | 0.06 |
| Niacinamide | 0.04 |
| Riboflavin | 0.3 |
| Biotin | 0.02 |
| Copper sulfate | 0.003 |
| Ammonium molybdate | 0.00120 |
| Ammonium vanadate | 0.003 |
| Mn chloride | 0.00002 |
| Sodium hyaluronate | 70 |
| Polyhexanide or polyhexamethylene biguanide | 0.1 |
| n-acetylcysteine | 500 |
| Hydroxyproline or proline | 35. |

* * * * *